(12) United States Patent
Schatz

(10) Patent No.: US 7,556,498 B2
(45) Date of Patent: Jul. 7, 2009

(54) MEDICAL CONTRA-ANGLE HANDPIECE

(75) Inventor: Norbert Schatz, Bürmoos (AT)

(73) Assignee: W&H Dentalwerk Bümoos GmbH, Burmoos (AT)

( * ) Notice: Subject to any disclaimer, the term of this patent is extended or adjusted under 35 U.S.C. 154(b) by 270 days.

(21) Appl. No.: 11/168,840

(22) Filed: Jun. 27, 2005

(65) Prior Publication Data
US 2006/0008769 A1    Jan. 12, 2006

(30) Foreign Application Priority Data
Jun. 28, 2004    (AT) .............................. A 1090/2004

(51) Int. Cl.
*A61C 1/08*    (2006.01)
(52) U.S. Cl. ..................................... 433/133; 433/114
(58) Field of Classification Search ................. 433/124, 433/125, 126, 103, 114, 133
See application file for complete search history.

(56) References Cited

U.S. PATENT DOCUMENTS

| | | | | |
|---|---|---|---|---|
| 319,110 | A * | 6/1885 | Miller | 433/126 |
| 2,093,682 | A * | 9/1937 | Levy | 433/124 |
| 2,135,933 | A * | 11/1938 | Blair | 601/89 |
| 4,278,428 | A * | 7/1981 | Straihammer et al. | 433/105 |
| 4,278,429 | A * | 7/1981 | Straihammer et al. | 433/126 |
| 4,568,642 | A | 2/1986 | DeForrest et al. | |
| 5,169,312 | A * | 12/1992 | Berlin | 433/123 |
| 5,328,369 | A * | 7/1994 | Bailey | 433/125 |
| 5,575,647 | A * | 11/1996 | Grubbs | 433/114 |
| 5,772,436 | A * | 6/1998 | Matsui et al. | 433/126 |
| 5,902,107 | A * | 5/1999 | Lowell | 433/130 |
| 6,168,433 | B1 * | 1/2001 | Hamlin | 433/125 |
| 6,305,935 | B1 * | 10/2001 | Cardarelli | 433/126 |

FOREIGN PATENT DOCUMENTS

| | | |
|---|---|---|
| AT | 408 514 | 12/2001 |
| WO | WO 03/105713 | 12/2003 |

* cited by examiner

*Primary Examiner*—Ralph A Lewis
(74) *Attorney, Agent, or Firm*—Klarquist Sparkman, LLP

(57) ABSTRACT

Medical, in particular dental, contra-angle handpieces for driving a dental instrument connected to the contra-angle handpiece with shafts arranged in the contra-angle handpiece for the transmission of the drive movement to the instrument. In order to achieve a reduction of sound emission and a reduction of the manufacturing and assembly costs while still incorporating the curvature of the outer sleeve of the contra-angle handpiece and the advantages which this entails, the contra-angle handpiece is equipped with a single-piece shaft which is essentially centered at the proximal end and the distal end of the outer sleeve, but runs eccentrically in a section of the outer sleeve between the proximal end and the distal end. The curvature of the outer sleeve of the contra-angle handpiece is in the range of about 8° to about 16°, and in some implementations, in the range of about 10° to about 14°.

20 Claims, 1 Drawing Sheet

MEDICAL CONTRA-ANGLE HANDPIECE

CROSS REFERENCE TO RELATED APPLICATION

The present application claims priority from pending Austrian Patent Application No. A 1090/2004, filed Jun. 28, 2004, which is incorporated herein by reference.

FIELD

The present application is concerned with medical, in particular dental, contra-angle handpieces for driving an instrument connected to the contra-angle handpiece with shafts arranged in the contra-angle handpiece for the transmission of the drive movement to the instrument.

DESCRIPTION OF PRIOR ART

Such a contra-angle handpiece is, for example, disclosed in AT 408.514 B. By contrast with straight handpieces, the outer sleeve of the contra-angle handpieces features a curvature, for the contra-angle handpieces submitted by the applicant preferably in the range of 18°-21°. For the user, this curvature is ergonomically advantageous and simplifies the viewing of the treatment site. The outer sleeve of the contra-angle handpiece contains, along with other equipment, the motor shafts, which transmit the drive movement of the respective drive unit, preferably an electric motor, to the instrument.

The disadvantage of such contra-angle handpieces is that, in order to overcome the curvature of the outer sleeve, in the area of their curvature the ends of the motor shafts must be connected by gearwheels. The manufacture and assembly of the shafts with the gearwheels is cost-intensive. Furthermore, during operation, due to the friction between the meshing gearwheels, losses occur in the transmission of the torque, as well as running noise, sensed by both the user and the patient as disturbing.

It would be beneficial to provide a contra-angle handpiece which still incorporates the curvature of the outer sleeve and the advantages which this entails while at the same time offering improved torque transmission, with reduced losses, reduced sound emission and less costly manufacturing and assembly.

SUMMARY

Disclosed below are representative embodiments that are not intended to be limiting in any way. Instead, the present disclosure is directed toward novel and nonobvious features, aspects, and equivalents of the embodiments of the contra-angle handpiece described below. The disclosed features and aspects of the embodiments can be used alone or in various novel and nonobvious combinations and sub-combinations with one another.

Surprisingly, a contra-angle handpiece with a single-piece shaft running through the entire contra-angle handpiece up to the head shaft, arranged in the head of the contra-angle handpiece, could be designed without having to eliminate the curvature of the outer sleeve. The single-piece shaft and, if necessary, the dog as a functional part of the single-piece shaft are essentially centered at the proximal end and the distal end of the outer sleeve, as compared with an eccentric arrangement in a section between the proximal end and the distal end. The curvature of the outer sleeve of the contra-angle handpiece is preferably in the range of about 8° to about 16°, with particular preference for the range of about 10° to about 14°.

In extensive practical trials, remarkably enough it could be demonstrated that implementations of a contra-angle handpiece offer the user the same advantages in terms of ergonomics and free viewing of the treatment site as the contra-angle handpieces known from the present state of the art. At the same time, a reduction of sound emission and improved torque transmission with low losses are achieved. Furthermore, the new contra-angle handpiece reduces the costs of manufacturing and assembly.

In a preferred embodiment, the center axis of the neck section of the outer sleeve and the center axis of the head enclose an angle of greater than or equal to about 90°, with a preferred value in the range of about 92° to about 95°, permitting greater convenience for the user in the handling of the contra-angle handpiece.

The foregoing and additional features and advantages of the disclosed embodiments will become more apparent from the following detailed description, which proceeds with reference to the following drawings.

DETAILED DESCRIPTION

Figure 1:
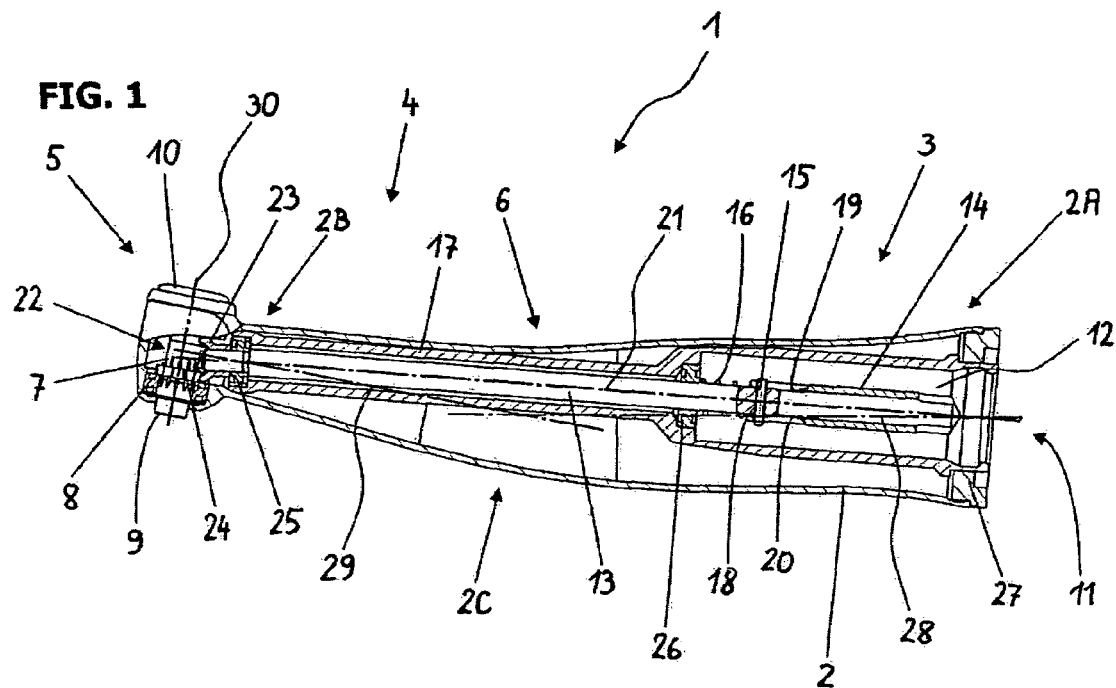
FIG. 1 illustrates a first embodiment of the contra-angle handpiece.

The outer sleeve 2 of contra-angle handpiece 1, in FIG. 1, is comprised of a handle 3, a neck section 4 and a contra-angle handpiece head 5. In the region of transition between the handle 3 and the neck section 4, the outer sleeve 2 features a curvature 6, which offers the user ergonomic advantages and also improved viewing of the treatment site.

In the contra-angle handpiece head 5 an instrument carrier 7 is arranged in a known manner as part of the head shaft 22, supported by two bearings, preferably rolling bearings 8 (due to the only partly removed outer sleeve, only one bearing can be seen). The instrument carrier 7 has an opening 9 on one side for inserting a dental instrument, for example a dental drill (not shown). On the side opposite the opening 9 of the head 5 is a pushbutton 10 for releasing the dental instrument from the instrument carrier 7.

At the proximal end 2A of the outer sleeve 2 is a coupling device 11 for connecting to a drive unit, preferably an electric motor. For the transmission of the drive movement from the motor to the dental instrument, a coupling tenon (not shown) is arranged in a known manner at the distal end of the drive unit and led into the cavity 12 of the contra-angle handpiece 1, so that the rotor shaft of the motor is connected to the shaft 13 of the contra-angle handpiece. The cavity 12 is formed by an enlargement of the inside diameter of the bearing sleeve 17 in its proximal section.

At the proximal end of the shaft 13 is a transverse bore 18 for taking up a straight grooved pin 15. With the use of the straight grooved pin 15, the dog 14 is connected to the shaft 13. Pin 15 passes through two longitudinal slits 19, 20 of the dog 14. The spring 16 preloads the dog 14 against the shaft 13 and the bearing sleeve 17. As a result of the two longitudinal slits 19, 20 the dog 14 can be displaced parallel to the center axis 21 of the shaft 13. This play ensures the secure coupling of the drive unit and the contra-angle handpiece 1, as well as the reliable transmission of the rotational movement and the torque from the rotor shaft to the shaft 13.

In some implementations, the transmission of the drive movement through the entire contra-angle handpiece 1 up to the head shaft 22 in the head 5 is implemented by one, single-piece rigid shaft 13. The shaft 13 is arranged in the contra-angle handpiece 1 so that it and the dog 14 as a part and functional extension of the shaft 13 are essentially centered at the proximal end 2A and at the distal end 2B of the outer sleeve 2. By contrast, at section 2C of the outer sleeve 2 between the proximal end 2A and the distal end 2B the shaft 13 is eccentrically arranged, i.e., it is off center and positioned closer to one side. At the distal end of the shaft 13 is a gearwheel 23, which meshes with a second gearwheel 24 of the head shaft 22 and transmits the drive movement to the head shaft 22 and the dental instrument fixed in the instrument carrier 7.

The shaft 13 is supported by the likewise single-piece designed bearing sleeve 17 by means of two rolling bearings 25, 26. The distal end of the bearing sleeve 17 is supported at the inner wall of the outer sleeve 2 and the proximal end at a threaded ring 27 as a part of the coupling 11.

Figure 2:
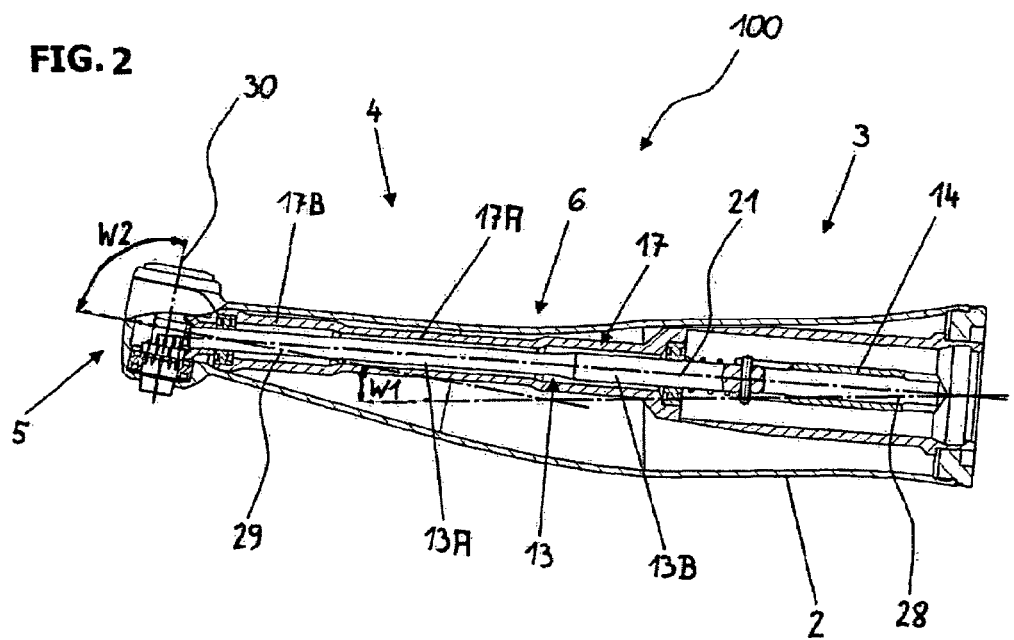
FIG. 2 illustrates a second embodiment of the contra-angle handpiece.

The contra-angle handpiece 100 illustrated in FIG. 2 corresponds in its design to the contra-angle handpiece 1 of FIG. 1, so that it is not necessary to repeat the detailed description here.

By contrast with FIG. 1, the shaft 13 and the bearing sleeve 17 of the contra-angle handpiece 100 are comprised of several sections 13A and 13B and 17A and 17B, respectively, with different diameters. Section 17A, with the smaller diameter, surrounds at least parts of section 13A, with the smaller diameter. The respective sections 13A and 17A with the smaller diameters are in the region of the curvature 6 of the outer sleeve 2, preferentially enabling greater curvature of the outer sleeve 2. The shaft 13 and the bearing sleeve 17 can of course embrace more than two sections, with different diameters.

In addition, FIG. 2 also gives information about the relevant angles between the individual components of the contra-angle handpiece 100, which apply analogously for the contra-angle handpiece 1 illustrated in FIG. 1.

The center axis 28 of the handle 3 and the center axis 29 of the neck section 4 enclose an angle W1 in the range of about 8° to about 16°, preferably in the range of about 10° to about 14°. The angle W1 is that angle which describes the curvature 6, important for the user. The angle W2 is formed by the center axis 29 of the neck section 4 and the center axis 30 of the head 5. The angle W2 is greater than or equal to about 90°, preferably in the range of about 92° to about 95°. The angle of inclination W2 of the head 5 in relation to the neck section 4 is in addition to the angle W1 of curvature 6, so that overall the contra-angle handpieces 1 and 100 offer the user the same advantages in terms of ergonomics and free viewing of the treatment site as the contra-angle handpieces known from the present state of the art.

The invention is not limited to the range of applications and the embodiments described, but contains all embodiments which do not entail changes of the fundamental character of the functional principle. Thus, for example, the term "single-piece shaft" also encompasses shafts comprised of several parts and preferably connected during assembly of the contra-angle handpiece, such as by form-fitting, in particular by a screw connection, so that the operation of the contra-angle handpiece is based on a functionally single-piece shaft without interconnected gearwheels or transmissions.

What is claimed is:

1. Contra-angle handpiece for driving a dental instrument connected to the contra-angle handpiece, the contra-angle handpiece comprising:
    an outer sleeve, said outer sleeve comprising a handle section, a neck section and a contra-angle handpiece head, wherein the handle section and the neck section are arranged at a nonzero first angle relative to each other and wherein the neck section and the contra-angle handpiece head are arranged at a nonzero second angle relative to each other,
    a head shaft having a transverse axis disposed in the contra-angle handpiece head for connection to the dental instrument,
    a substantially straight shaft for the transmission of drive movement through the handle section and the neck section to the head shaft,
    wherein the substantially straight shaft defines a single straight first longitudinal axis and has a proximal end, a distal end, and an intermediate section between the proximal end and the distal end, wherein the distal end is connected to the head shaft and wherein the distal end and the proximal end are substantially centrally spaced in the outer sleeve, and wherein the intermediate section is arranged eccentrically in the outer sleeve, and
    a coupling device positioned at an end of the contra-angle handpiece. opposite the contra-angle handpiece head, for connecting the contra-angle handpiece to an external drive unit, the coupling device having a second longitudinal axis that is a continuation of the first longitudinal axis of the substantially straight shaft so that drive movement from the coupling device to the head shaft is along a single straight longitudinal axis.

2. Contra-angle handpiece in accordance with claim 1, wherein, viewing a longitudinal section, the substantially straight shaft is approximately equally spaced between adjacent portions of the outer sleeve at the proximal end and at the distal end, and wherein along a section of the substantially straight shaft between the proximal end and the distal end, the substantially straight shaft is spaced closer to one adjacent portion of the outer sleeve than an opposite adjacent portion.

3. Contra-angle handpiece in accordance with claim 1, wherein the first angle is about 8° to about 16° and is defined between a center axis of a handle section and a center axis of a neck section.

4. Contra-angle handpiece in accordance with claim 1, wherein the first angle is about 10° to about 14° and is defined between a center axis of a handle section and a center axis of a neck section.

5. Contra-angle handpiece in accordance with claim 1, with the substantially straight shaft having a first diameter along a first section and a second diameter along a second section.

6. Contra-angle handpiece in accordance with claim 5, with the second diameter being smaller than the first diameter and the second section of substantially straight shaft with the smaller diameter being arranged in the region of the nonzero first angle between the handle section and the neck section.

7. Contra-angle handpiece in accordance with claim 5, with the substantially straight shaft arranged in a bearing sleeve and the bearing sleeve also having a first diameter and a second diameter smaller than the first diameter, with the section of the bearing sleeve having the smaller diameter surrounding at least part of the shaft section with the smaller diameter.

8. Contra-angle handpiece in accordance with claim 6, with the substantially straight shaft arranged in a bearing sleeve and the bearing sleeve also having a first and a second, smaller, diameter, with the section of the bearing sleeve having the smaller diameter surrounding at least parts of the shaft section with the smaller diameter.

9. Contra-angle handpiece in accordance with claim 1, wherein a center axis of a neck section of the outer sleeve and a center axis of the head define the nonzero second angle to be greater than or equal to about 90°.

10. Contra-angle handpiece in accordance with claim 9, wherein the nonzero second angle is about 92° to about 95°.

11. Contra-angle handpiece in accordance with claim 1, wherein the substantially straight shaft is a substantially rigid shaft.

12. Contra-angle handpiece in accordance with claim 1, wherein the straight first longitudinal axis defines the rotational axis of the substantially straight shaft.

13. Contra-angle handpiece in accordance with claim 1, wherein the substantially straight shaft is a single-piece shaft.

14. Contra-angle handpiece in accordance with claim 1, wherein the substantially straight shaft is comprised of multiple parts connected to each other without interconnected gear wheels or transmissions and the straight first longitudinal axis defines a common rotational axis for the multiple parts.

15. Contra-angle handpiece in accordance with claim 1, wherein the substantially straight shaft is supported by only two roller bearings.

16. Contra-angle handpiece in accordance with claim 1, wherein the intermediate section is arranged eccentrically in the region of the nonzero first angle of the outer sleeve between the handle section and the neck section.

17. Contra-angle handpiece in accordance with claim 1, wherein the nonzero first angle comprises a curvature, which connects the handle section to the neck section.

18. Contra-angle handpiece in accordance with claim 1, wherein the substantially straight shaft comprises a dog.

19. Contra-angle handpiece in accordance with claim 18, wherein the dog is displaceable parallel to first longitudinal axis of the substantially straight shaft.

20. Contra-angle handpiece in accordance with claim 18, wherein the dog comprises a hollow shaft.

* * * * *